United States Patent [19]

Haugwitz et al.

[11] 4,156,006

[45] * May 22, 1979

[54] VINYL SULFIDE DERIVATIVES OF BENZIMIDAZOLES

[75] Inventors: Rudiger D. Haugwitz; Barbara V. Maurer, both of Titusville, N.J.

[73] Assignee: E. R. Squibb & Sons, Inc., Princeton, N.J.

[*] Notice: The portion of the term of this patent subsequent to Sep. 6, 1994, has been disclaimed.

[21] Appl. No.: 868,148

[22] Filed: Jan. 9, 1978

[51] Int. Cl.² .................. C07D 235/32; A61K 31/415
[52] U.S. Cl. .................................. 424/273 R; 548/306
[58] Field of Search ...................... 548/306; 424/273 R

[56] References Cited

U.S. PATENT DOCUMENTS

| | | | |
|---|---|---|---|
| 3,574,845 | 4/1971 | Actor et al. | 548/306 |
| 3,578,676 | 5/1971 | Dunn | 548/306 |
| 3,682,952 | 8/1972 | Actor et al. | 548/306 |
| 3,694,455 | 9/1972 | Dunn | 548/306 |
| 3,738,993 | 6/1973 | Haugwitz et al. | 548/333 |
| 3,915,986 | 10/1975 | Gyurik et al. | 548/306 |
| 3,928,375 | 12/1975 | Düwel et al. | 548/306 |
| 3,929,821 | 12/1975 | Beard et al. | 548/306 |
| 3,929,822 | 12/1975 | Beard et al. | 548/306 |
| 3,929,823 | 12/1975 | Beard et al. | 548/306 |
| 3,929,824 | 12/1975 | Beard et al. | 548/306 |
| 3,935,209 | 1/1976 | Beard et al. | 548/306 |
| 3,954,791 | 5/1976 | Loewe et al. | 548/306 |
| 3,965,113 | 6/1976 | Beard et al. | 548/306 |
| 3,969,526 | 7/1976 | Gyurik et al. | 548/306 |
| 4,002,640 | 1/1977 | Beard et al. | 548/306 |
| 4,005,202 | 1/1977 | Beard et al. | 548/306 |
| 4,046,908 | 9/1977 | Haugwitz et al. | 548/306 |
| 4,093,732 | 6/1978 | Haugwitz et al. | 424/273 R |

FOREIGN PATENT DOCUMENTS 2363351  7/1974  Fed. Rep. of Germany .......... 548/306

*Primary Examiner*—Alan L. Rotman
*Attorney, Agent, or Firm*—Lawrence S. Levinson; Merle J. Smith; Burton Rodney

[57] ABSTRACT

Vinyl sulfide derivatives of benzimidazoles are provided having the structure

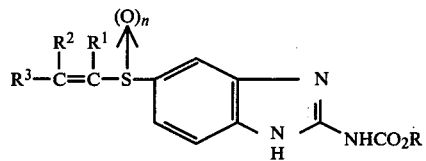

wherein R is lower alkyl or phenyl-lower alkyl, $R^1$ is lower alkyl, $R^2$ is hydrogen or lower alkyl, or $R^1$ and $R^2$ may be taken together with the carbons to which they are attached to form a cycloalkenyl ring, $R^3$ is hydrogen or lower alkyl, and n is 0 or 1. These compounds are useful as anthelmintic agents.

7 Claims, No Drawings

VINYL SULFIDE DERIVATIVES OF BENZIMIDAZOLES

BACKGROUND OF THE INVENTION

Various benzimidazole compounds are known for their use as anthelmintic agents, such as disclosed in U.S. Pat. Nos. 3,929,821, 3,929,822, 3,929,823, 3,929,824, 3,935,209, 3,965,113, 4,002,640 and 4,005,202 all to Beard et al. and assigned to Syntex; 3,574,845 and 3,682,952 to Actor, 3,578,676 and 3,694,455 to Dunn, 3,915,986 and 3,969,526 to Gyurik, all assigned to Smith Kline; 3,738,993 to Haugwitz et al.

U.S. Pat. No. 4,002,640 discloses benzimidazole compounds which have the structure

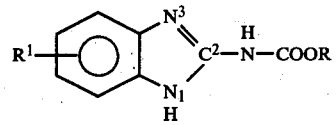

wherein R is lower alkyl having 1 to 4 carbon atoms, $R^1$ may be $-SR^5$, and $R^5$ may be lower alkenyl, wherein the double bond is not on the α-carbon. Specific compounds disclosed include 5(6)-(prop-2-en-1-ylthio)-2-carbomethoxyaminobenzimidazole, and 5(6)-(prop-2-en-1-ylsulfinyl)-2-carbomethoxyaminobenzimidazole. These compounds as well as the benzimidazoles disclosed in all of the aforementioned patents are said to be active perorally in the treatment of helminthiasis.

U.S. Pat. Nos. 3,954,791 to Loewe et al and 3,928,375 to Duwel et al, both assigned to Hoechst disclose 2-carbalkoxy-amino-benzimidazole-5(6)-phenyl ethers (and thioethers) which are said to be active perorally as well as subcutaneously.

DESCRIPTION OF THE INVENTION

The present invention relates to vinyl sulfide derivatives of benzimidazoles having the structure

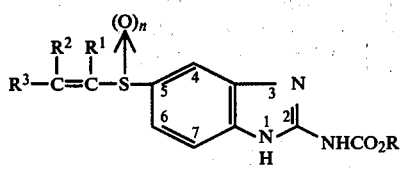

wherein R is lower alkyl or phenyl-lower alkyl, $R^1$ is lower alkyl, $R^2$ is hydrogen or lower alkyl, or $R^1$ and $R^2$ may be taken together with the carbons to which they are attached to give a cycloalkenyl ring containing 3 to 10 carbons, preferably 4 to 8 carbons, optimally 5 to 7 carbons, $R^3$ is hydrogen or lower alkyl, and n is 0 or 1.

The term "lower alkyl" as used herein includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "phenyl lower alkyl" as used herein refers to lower alkyl groups as discussed above having a phenyl substituent, such as benzyl.

The term "cycloalkenyl" includes cyclic hydrocarbon groups containing 3 to 10 carbons. Examples of suitable cycloalkenyl groups include cyclopropenyl, cyclobutenyl, cyclohexenyl, cycloheptenyl, cyclononenyl and cyclodecenyl. In the above cycloalkenyl rings, the double bond is at the alpha position in the ring.

Preferred are those compounds wherein R is methyl, ethyl, propyl or benzyl, n is 0 or 1, $R^1$ and $R^2$ are taken together to form a cyclohexen-1-yl ring or a cyclopenten-1-yl ring, or $R^1$ is methyl, ethyl or n-propyl and $R^2$ is hydrogen, methyl or ethyl, and $R^3$ is hydrogen.

Examples of preferred compounds falling within the present invention include the following.

| | | | | | | |
|---|---|---|---|---|---|---|
| | R | $R^1$ | ($R^1 + R^2$) | $R^2$ | $R^3$ | n |
| 1. | $CH_3$ | $CH_3$ | | H | H | 0 |
| 2. | $C_2H_5$ | $C_2H_5$ | | $CH_3$ | H | 0 |
| 3. | $C_2H_4C_6H_5$ | | $C_4H_8$ | | H | 0 |
| 4. | $CH_3$ | | $C_3H_6$ | | H | 0 |
| 5. | $CH_3$ | $C_3H_7$ | | $C_2H_5$ | H | 0 |
| 6. | $C_2H_5$ | | $C_3H_6$ | | H | 1 |
| 7. | $CH_3$ | | $C_3H_6$ | | H | 1 |
| 8. | $C_2H_5$ | $C_2H_5$ | | $CH_3$ | H | 1 |
| 9. | $CH_3$ | $C_3H_7$ | | $C_2H_5$ | H | 1 |
| 10. | $CH_3$ | | $C_2H_4$ | | $CH_3$ | 1 |
| 11. | $CH_3$ | | $C_6H_{12}$ | | H | 0 |
| 12. | $CH_3$ | | $C_8H_{16}$ | | H | 1 |
| 13. | $C_2H_5$ | $C_5H_{11}$ | | H | $C_2H_5$ | 0 |
| 14. | $CH_2C_6H_5$ | $C_2H_5$ | | $CH_3$ | $CH_3$ | 1 |

The compounds of structure I may be prepared as follows.

The vinyl thiol II is prepared by using the methods published by Mayer [J. Praktische Chemie 34, 116 (1966); Chem. Ber. 96, 3096 (1963); 99, 1771 (1966); Angew. Chemie Internat. Ed. 1, 217 (1962)]. The alkali salt of II is then reacted with 5-chloro-2-nitroaniline III to furnish IV. The reaction can be carried out in solvents such as alcohols, acetonitrile or glyme at temperatures ranging from about 25° to about 100° for periods of about 30 minutes to 10 hours.

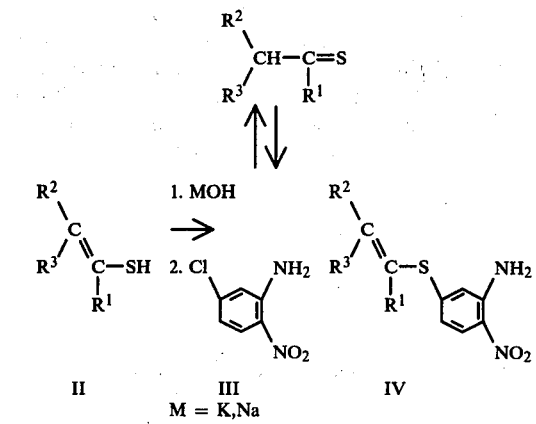

The compounds of structure IV where $R^1$ and $R^2$ form a cycloalkene may be prepared as reported by Seebach et al. [Chem. Ber. 107, 847 (1964)]. Reaction of the lithilated vinyl derivative V with a disulfide VI yields IV.

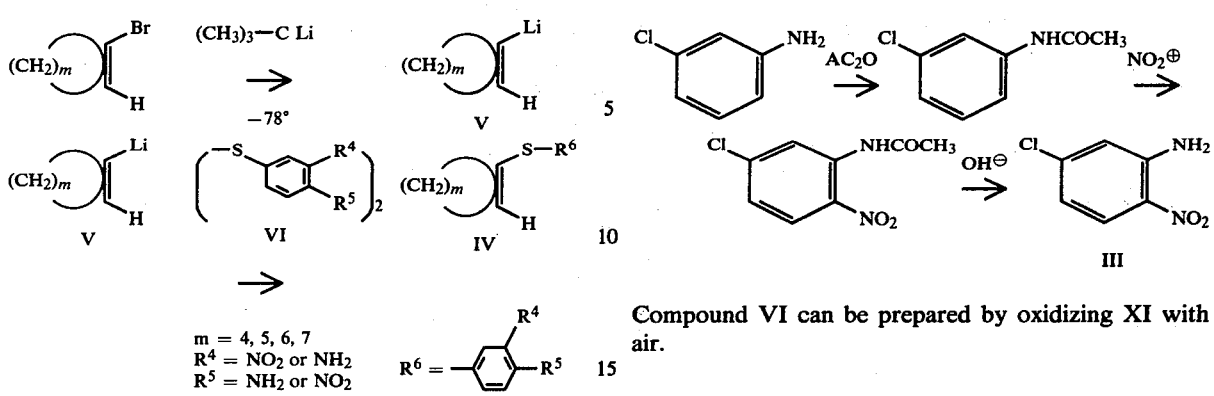

m = 4, 5, 6, 7
R⁴ = NO₂ or NH₂
R⁵ = NH₂ or NO₂

$R^6 = $ 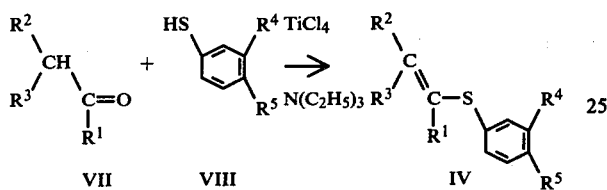

Mukaiyama [Chem. Letters 479 (1973)] describes an additional route toward IV by reacting a carbonyl compound VII with a thiol VIII in the presence of TiCl₄.

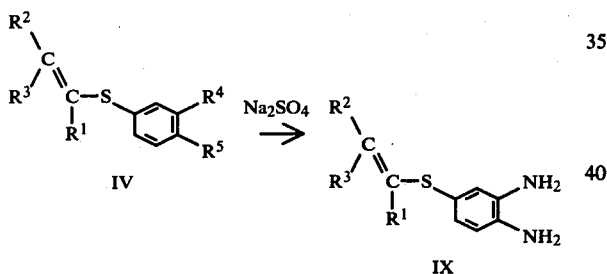

Vinyl sulfides IV are conveniently reduced to the requisite o-phenylenediamines IX by using aqueous Na₂S₂O₄.

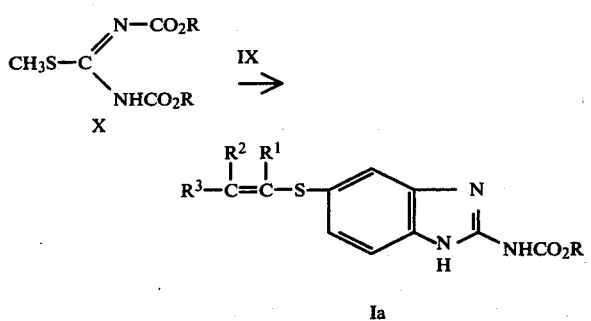

The final step in the synthesis of I where n=0, namely ring-closure of IX to furnish Ia, can be achieved in various ways. Refluxing IX with the isolated thiourea derivative X will yield Ia. The preferred method of preparing Ia is by forming X in situ and then without isolating it, adding IX and refluxing it for 30 minutes to 5 hours, to yield the desired product.

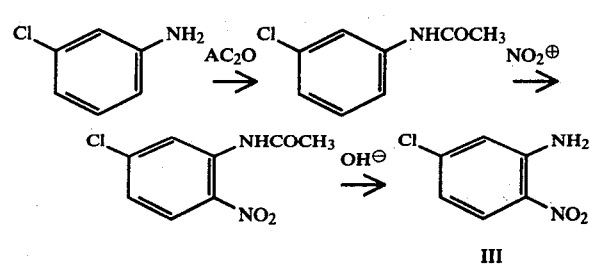

Compound III can be prepared by the sequence depicted below:

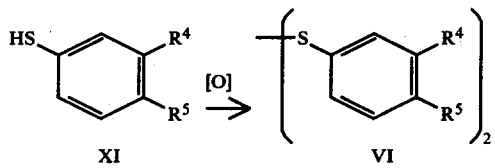

Compound VI can be prepared by oxidizing XI with air.

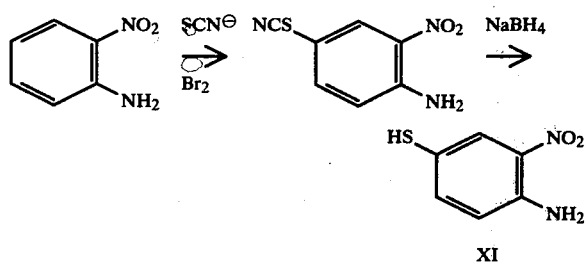

Compound XI is prepared by the route outlined below:

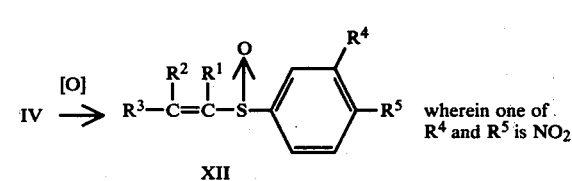

The sulfides of structure IV are converted to the corresponding sulfoxides by oxidizing agents such as hydrogen peroxide, peracids (e.g., peracetic acid, m-chloroperbenzoic acid), manganese dioxide, sodium metaperiodate as outlined by Sandler and Caro (*Organic Functional Group Preparations*, 1968, p. 493).

$$IV \xrightarrow{[O]} R^3-\overset{R^2}{\underset{}{C}}=\overset{R^1}{\underset{}{C}}-\overset{O}{\underset{}{S}}-\text{Ar}(R^4)(R^5)$$

XII   wherein one of R⁴ and R⁵ is NO₂

The resulting sulfoxides XII may be purified by crystallization and then reduced to the corresponding o-phenylenediamine XIII. Chemical reduction may be used. For the chemical reduction, the procedure outlined by Sandler and Caro (*Organic Functional Group Preparations*, 1968, pp. 339-340) is preferred. The final step in the synthesis of sulfoxides of formula I (n=1), namely ring closure of XIII to furnish Ib, can be achieved in various ways. Whereas refluxing of XIII with the isolated thiourea derivative XIV in alcohols such as methanol or ethanol will furnish Ib, the preferred method of preparing I is by forming XIV in situ and then without isolating it adding XIII and refluxing it for 30 minutes to 5 hours to yield the desired product.

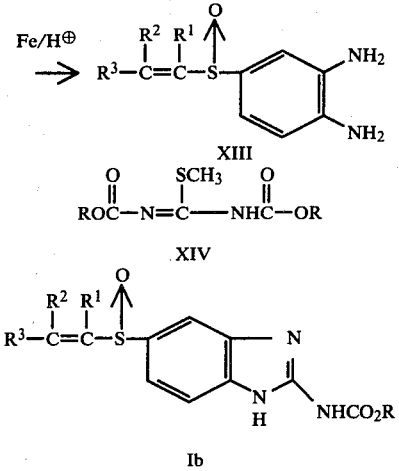

Alternatively, sulfoxides of structure Ib may be prepared directly from the sulfides (Ia) by oxidizing the sulfides with NaIO₄.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5–25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%.

Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

[5-(1-Cyclohexen-1-ylthio)-1H-benzimidazol-2-yl]carbamic acid, methyl ester

A. 5-(1-Cyclohexen-1-ylthio)-2-nitrobenzene-amine

To a solution of 6.9 g (0.04 mole) of 5-chloro-2-nitroaniline in 50 ml of absolute ethanol there is added 6.0 g of the potassium salt of 1-cyclohexene-1-thiol [J. Praktische Chemie 34, 116 (1966)]. The mixture is heated on the steam bath for 0.5 hour, filtered and the filtrate is reduced in volume in vacuo. The resulting solid is filtered off and crystallized from absolute ethanol to yield 5.3 g, m.p. 100°–102°.

B. 5-(1-Cyclohexen-1-ylthio)-o-phenylenediamine

To a suspension of 3.5 g (0.014 mole) of 5-(1-cyclohexen-1-ylthio)-2-nitrobenzene-amine in 125 ml of absolute ethanol under $N_2$ there is added a solution of 8.4 g of $Na_2S_2O_4$, 8.4 ml of concentrated aqueous ammonia and 52.5 ml of water. The mixture is refluxed for 15 minutes and an additional 0.8 g of $Na_2S_2O_4$ is added. After an additional 15 minutes reflux period TLC (silica, $Et_2O$) shows no starting material present. The ethanol is removed in vacuo; the aqueous residue is taken to pH 12 with 50% aqueous NaOH and then extracted with $CH_2Cl_2$. The organic extracts are combined, dried (MgSO$_4$) and evaporated to give an oil which is used immediately in the following reaction.

C. [5-(1-Cyclohexen-1-ylthio)-1H-benzimidazol-2-yl]carbamic acid, methyl ester

To a solution of the above diamine in 50 ml of methanol there is added 1 ml of acetic acid and 2.8 g (0.014 mole) of 1,3-bis(methoxycarbonyl)-5-methylisothiourea and the resulting mixture is refluxed for 2 hours. The methanol is removed in vacuo and water is added. The resulting solid is filtered off, dried and crystallized from glyme-acetonitrile (1:1) to yield 2.9 g of the title compound, m.p. 224°–226° C. (dec.).

EXAMPLE 2

[5-(1-Cyclopenten-1-ylthio)-1H-benzimidazol-2-yl]carbamic acid, methyl ester

Following the procedure of Example 1, but substituting for cyclohexanone, cyclopentanone, the title compound is outlined.

EXAMPLE 3

[5-(1-Cyclohepten-1-ylthio)-1H-benzimidazol-2-yl]carbamic acid, methyl ester

Following the procedure of Example 1 but substituting for cyclohexanone, cycloheptanone, the title compound is obtained.

EXAMPLE 4

[5-(4-Hepten-1-ylthio)-1H-benzimidazol-2-yl]carbamic acid, methyl ester

Following the procedure of Mayer [Ber. 99, 1771 (1966)] for preparing heptan-4-thione and substituting it for the 1-cyclohexene-1-thiol used in Example 1, the title compound is obtained.

EXAMPLE 5

[5-(1-Cyclohexen-1-ylsulfinyl)-1H-benzimidazol-2-yl]carbamic acid, methyl ester

A. 4-(1-Cyclohexen-1-ylthio)-2-nitrobenzene-amine

To 500 ml of dry tetrahydrofuran under N$_2$ there is added 5.0 g of cyclohexanone and then 5.5 ml of TiCl$_4$. Then there is added a mixture of 11.0 ml of triethylamine and 8.5 g of 3-amino-4-nitrobenzenethiol in 105 ml of dry tetrahydrofuran and the mixture is stirred overnight at room temperature. Then there is added 300 ml of H$_2$O and the mixture is extracted with dichloromethane. The organic layers are combined, dried (MgSO$_4$) and evaporated in vacuo. The residue is chromatographed on silica gel. Elution with 1:1 PE-Et$_2$O yields 2.8 g of 4-(1-cyclohexen-1-ylthio)-2-nitrobenzene-amine, m.p. 93°–95° C.

B. 4-(1-Cyclohexen-1-ylsulfinyl)-2-nitrobenzene-amine

To a solution of 2.5 g (0.01 mole) of the benzeneamine obtained from part A in 50 ml of methanol under N$_2$ there is added a solution of 2.2 g NaIO$_4$ in 20 ml of H$_2$O at 0°–5° C. for 30 hours. The mixture is then extracted with dichloromethane. The organic layers are combined, dried, and evaporated. The residue is crystallized from acetonitrile to give 2.2 g, m.p. 139°–140° C. of the sulfoxide.

C. [5-(1-Cyclohexen-1-ylsulfinyl)-o-phenylenediamine]

To a suspension of 2.0 g (0.0075 mole) of 4-(1-cyclohex-1-ylsulfinyl)-2-nitrobenzeneamine in 75 ml of absolute ethanol under N$_2$ there is added a solution of 4.9 g of Na$_2$S$_2$O$_4$, 4.9 ml of concentrated ammonia and 30 ml of H$_2$O. The mixture is refluxed for 15 minutes and an additional 0.4 g of Na$_2$S$_2$O$_4$ is added. After an additional 15 minutes reflux period the ethanol is removed in vacuo. The aqueous residue is taken to pH 12 with 50% aqueous NaOH and then extracted with dichloromethane. The organic extracts are dried (MgSO$_4$) and evaporated to give an oil which is used immediately in the following reaction.

D. [5-(1-cyclohexen-1-ylsulfinyl)-1H-benzimidazol-2-yl]carbamic acid, methyl ester To a solution of the above diamine in 25 ml of methanol there is added 0.5 ml of acetic acid and 1.5 g of 1,3-bis(methoxy carbonyl)-5-methylisothiourea and the resulting mixture is refluxed for 3 hours. The methanol is removed in vacuo and water is added. The resulting solid is filtered off and crystallized from acetonitrile to yield 1.05 g of the title compound, m.p. 228°–230° C. (dec.).

EXAMPLE 6

[5-(1-Cyclopenten-1-ylsulfinyl)-1H-benzimidazol-2-yl]carbamic acid, methyl ester Following the procedure of Example 5, but substituting for cyclohexanone, cyclopentanone, the title compound is obtained.

EXAMPLE 7

[5-(1-Cyclohepten-1-ylsulfinyl)-1H-benzimidazol-2-yl]carbamic acid, methyl ester Following the procedure of Example 5, but substituting for cyclohexanone, cycloheptanone, the title compound is obtained.

EXAMPLE 8

[5-(4-Hepten-1-ylsulfinyl)-1H-benzimidazol-2-yl]carbamic acid, methyl ester

The sulfide of Example 4 is oxidized with NaIO$_4$ to give the title sulfoxide.

EXAMPLE 9

[5-(3-Penten-1-ylthio)-1H-benzimidazol-2-yl]carbamic acid, methyl ester

Following the procedure set out in Example 5A, C and D except substituting 3-pentanone for cyclohexanone, the title compound is obtained.

EXAMPLE 10

[5-(5-Nonen-1-ylthio)-1H-benzimidazol-2-yl]carbamic acid, methyl ester

Following the procedure set out in Example 5A, C and D except substituting 5-nonanone for cyclohexanone, the title compound is obtained.

EXAMPLES 11 TO 21

Following the procedure of Example 1 but substituting for 1-cyclohexene-1-thiol the compound shown in Column I of Table I below, and substituting for 1,3-bis(methoxycarbonyl)-5-methylisothiourea the compound shown in Column II, the sulfide derivatives of benzimidazoles as shown in Column III are obtained.

TABLE I

| | Column I | | | | Column II | Column III | |
|---|---|---|---|---|---|---|---|
| | $\begin{array}{c}R^2\\ \phantom{R}\diagdown\\ \phantom{RR}C=C-SH\\ \phantom{R}\diagup \phantom{RR} |\\ R^3 \phantom{RRR} R^1\end{array}$ | | | | $\begin{array}{c}\phantom{RR}N-CO_2R\\ \phantom{RR}\parallel\\ CH_3S-C\\ \phantom{RRR}\diagdown\\ \phantom{RRRR}NHCO_2R\end{array}$ | $R^2\diagdown\phantom{R}C=C-S-\text{(benzimidazole)}-NHCO_2R$ | |
| Ex. No. | (R¹+ R²) | R¹ | R² | R³ | R | R¹ R² R³ | R |
| 11. | — | CH₃ | H | H | CH₃ | | |
| 12. | — | C₂H₅ | CH₃ | H | C₂H₅ | as per Column I | as per Column II |
| 13. | C₄H₈ | — | — | CH₃ | C₂H₄C₆H₅ | | |
| 14. | C₃H₆ | — | — | C₂H₅ | CH₃ | | |
| 15. | — | C₃H₇ | C₂H₅ | H | C₂H₅ | | |
| 16. | C₃H₆ | — | — | CH₃ | C₂H₅ | | |
| 17. | C₃H₆ | — | — | CH₃ | CH₃ | | |
| 18. | — | C₂H₅ | CH₃ | C₂H₅ | C₂H₅ | | |
| 19. | — | C₃H₇ | C₂H₅ | H | CH₃ | | |
| 20. | C₂H₄ | — | — | CH₃ | CH₃ | | |
| 21. | C₃H₆ | — | — | H | CH₂C₆H₅ | | |

EXAMPLES 22 TO 32

Following the procedure of Example 8, the sulfides of Examples 11 to 21 shown in Column I of Table II below are oxidized to give the corresponding sulfoxides.

TABLE II

| | Column I | | | | | Column II | | | | |
|---|---|---|---|---|---|---|---|---|---|---|
| Ex. No. | (R¹ + R²) | R¹ | R² | R³ | R | (R¹ + R²) | R¹ | R² | R³ | R |
| 22. | — | CH₃ | H | H | CH₃ | | | | | |
| 23. | — | C₂H₅ | CH₃ | H | C₂H₅ | as per Column I | | | | |
| 24. | C₄H₈ | — | — | CH₃ | C₂H₄C₆H₅ | | | | | |
| 25. | C₃H₆ | — | — | C₂H₅ | CH₃ | | | | | |
| 26. | — | C₃H₇ | C₂H₅ | H | C₂H₅ | | | | | |
| 27. | C₃H₆ | — | — | CH₃ | C₂H₅ | | | | | |
| 28. | C₃H₆ | — | — | CH₃ | CH₃ | | | | | |
| 29. | — | C₂H₅ | CH₃ | C₂H₅ | C₂H₅ | | | | | |
| 30. | — | C₃H₇ | C₂H₅ | H | CH₃ | | | | | |
| 31. | C₂H₄ | — | — | CH₃ | CH₃ | | | | | |
| 32. | C₃H₆ | — | — | H | CH₂C₆H₅ | | | | | |

What is claimed is:

1. A compound of the structure

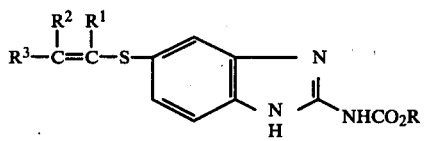

wherein R is lower alkyl containing 1 to 7 carbons or phenyl-lower alkyl containing 1 to 7 carbons in the alkyl group, R¹ and R² are taken together with the carbons to which they are attached to form a cycloalkene ring containing from 3 to 10 carbons, and R³ is hydrogen or lower alkyl containing from 1 to 7 carbons.

2. The compound as defined in claim 1 wherein R is lower alkyl or benzyl.

3. The compound as defined in claim 1 having the name [5-(1-cyclohexen-1-ylthio)-1H-benzimidazol-2-yl]carbamic acid, methyl ester.

4. An anthelmintic composition comprising an effective amount of a compound as defined in claim 1, and a pharmaceutically acceptable carrier therefor.

5. A method for treating helminthiasis which comprises administering to a mammalian host an effective amount of the composition as defined in claim 4.

6. The method as defined in claim 5 wherein said composition is administered orally.

7. The method as defined in claim 5 wherein said composition is administered parenterally.

UNITED STATES PATENT OFFICE
CERTIFICATE OF CORRECTION

Patent No. 4,156,006            Dated May 22, 1979

Inventor(s) Rudiger D. Haugwitz et al.

It is certified that error appears in the above-identified patent and that said Letters Patent are hereby corrected as shown below:

Column 2, in the reaction at the bottom of the column

" 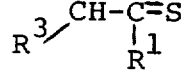 " should be placed above structure II.

Column 5, at the top of the column, "XII" should be placed before " $Fe/H^{\oplus}$  ".

Signed and Sealed this

*Twenty-fifth* Day of *September 1979*

[SEAL]

Attest:

Attesting Officer      LUTRELLE F. PARKER
*Acting Commissioner of Patents and Trademarks*